United States Patent [19]

Angelastro et al.

[11] Patent Number: 4,966,898

[45] Date of Patent: Oct. 30, 1990

[54] 4-SUBSTITUTED 17β-(CYCLOPROPYLAMINO)ANDROST-5-EN-3β-OL AND RELATED COMPOUNDS USEFUL AS $C_{17-20}$ LYASE INHIBITORS

[75] Inventors: Michael R. Angelastro, Loveland; Thomas R. Blohm, Cincinnati, both of Ohio

[73] Assignee: Merrell Dow Pharmaceuticals Inc., Cincinnati, Ohio

[21] Appl. No.: 394,025

[22] Filed: Aug. 15, 1989

[51] Int. Cl.$^5$ ..................... A61K 31/56; A61K 31/66
[52] U.S. Cl. ..................... 514/182; 514/177; 552/522
[58] Field of Search ............... 514/177, 178; 540/95; 552/522; 518/182

[56] References Cited

U.S. PATENT DOCUMENTS 3,097,200  7/1963  Kinel ..................... 540/95
3,107,254  10/1963  Lednicer ..................... 552/522

FOREIGN PATENT DOCUMENTS 0288053  10/1988  European Pat. Off. .
1027746  4/1966  United Kingdom .

OTHER PUBLICATIONS

Chemical Abstracts: vol. 111; 7670n, (1989).
Davis et al., *J. Chem. Soc., C, Org.*, 19, 1688, (1966).
B. J. Taylor, M. S. Thesis, Massachusetts Institute of Technology, 1985, pp. 2, 24–26.

*Primary Examiner*—Joseph A. Lipovsky
*Assistant Examiner*—Kevin E. Weddington
*Attorney, Agent, or Firm*—John J. Kolano

[57] ABSTRACT

This invention is directed to 4-substituted 17β-(cyclopropylamino)androst-5-en-3β-ol and related compounds and also to a method for using such compounds in the treatment of androgen-dependent disorders. The compounds are prepared by the hydride reduction of an appropriate steroidal imine or enamine.

8 Claims, No Drawings

4-SUBSTITUTED 17β-(CYCLOPROPYLAMINO)ANDROST-5-EN-3β-OL AND RELATED COMPOUNDS USEFUL AS $C_{17-20}$ LYASE INHIBITORS

The present invention is directed to 4-substituted 17β-(cyclopropylamino)androst-5-en-3β-ols and related compounds and also to a method for using such compounds in the treatment of androgen-dependent disorders. More particularly, the present invention is directed to a group of compounds having the following general formula:

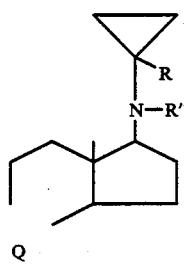

wherein R is hydrogen or methyl; R' is hydrogen, $C_1$–$C_4$ alkyl or cyclopropyl; and Q is

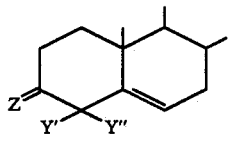

or

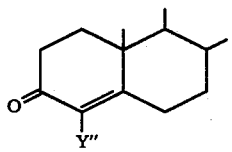

wherein Z is =O, β—OH or β—OZ' wherein Z' is alkanoyl of 1–10 carbon atoms or substituted $C_{2-4}$ alkanyol wherein the substituent is cyclopentane or benzene; Y' is hydrogen or halogen; and Y" is methyl or halogen. In the above structural formula, Z is shown as a divalent group and, in those definitions of Z which provide for only a single substituent (β), the second valence is occupied by hydrogen. Examples of the alkanoyl groups containing 1–10 carbon atoms are acetyl, propionyl, butanoyl, and decanoyl; examples of the substituted $C_{2-4}$ alkanoyl groups are cyclopentanepropionyl and benzenepropionyl. The halogen atoms referred to above can be fluorine, chlorine or bromine. Preferred compounds are those in which Q has structure I and, more particularly, those compounds in which Q has structure I and Y' and Y" are both halogen. A still further preferred group of compounds are those wherein Q has structure I and Y' and Y" are both fluorine.

Acid addition salts of the aforesaid compounds with pharmaceutically acceptable acids are equivalent to the above amines for the purposes of this invention. Illustrative of such salts are the salts with inorganic acids such as, for example, hydrochloric, hydrobromic, sulfuric, phosphoric and like acids; with organic carboxylic acids such as, for examples, acetic, propionic, glycolic, lactic, pyruvic, malonic, succinic, fumaric, malic, tartaric, citric, ascorbic, maleic, hydroxymaleic and dihydroxymaleic, benzoic, phenylacetic, 4-aminobenzoic, 4-hydroxybenzoic, anthranilic, cinnamic, salicylic, 4-aminosalicylic, 2-phenoxybenzoic, 2-acetoxybenzoic, mandelic and like acids; and with organic sulfonic acids such as methanesulfonic acid and p-toluenesulfonic acids.

Examples of specific compounds within the scope of the present invention are the following:
17β-(Cyclopropylamino)-4,4-difluoroandrost-5-en-3β-ol.
4,4-Difluoro-17β-(1-methylcyclopropylamino)androst-5-en-3β-ol.
3β-Acetoxy-17β-(cyclopropylamino-4,4-difluoroandrost-5-ene.
4,4-Difluoro-17β-[N-methyl(cyclopropylamino)]androst-5-en-3β-ol.
17β-(Cyclopropylamino)-4,4-difluoroandrost-5-en-3-one.
17β-(Cyclopropylamino)-4,4-dichloroandrost-5-en-3β-ol.
17β-(Cyclopropylamino)-4β-fluoroandrost-5-en-3β-ol.
17β-(Cyclopropylamino)-4β-methylandrost-5-en-3β-ol.
17β-(Cyclopropylamino)-4-fluoroandrost-4-en-3-one.
17β-(Cyclopropylamino)-4-methylandrost-4-en-3-one.

The compounds of the present invention are conveniently prepared by the reduction of an appropriate steroidal imine or enamine, wherein the compound used is a 3-hydroxy or 3-alkanoylhydroxy-$\Delta^5$-steroid, with a hydride reducing agent. Where the starting material is an imine, the reaction can be illustrated as follows:

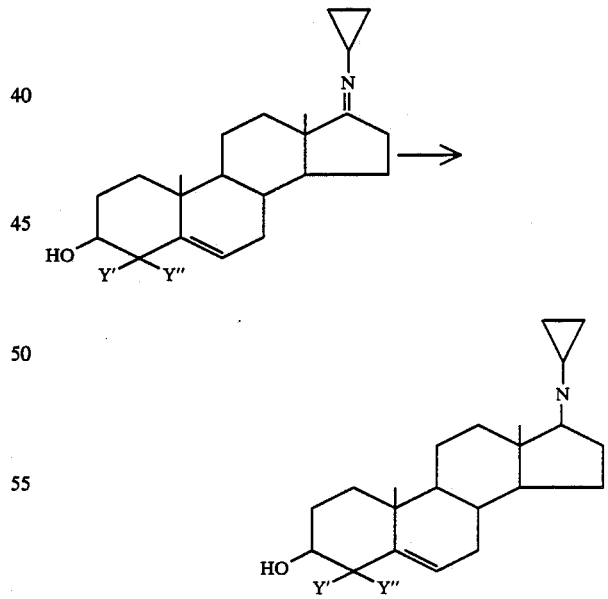

In this case, the reduction is carried out using a hydride reducing agent, preferably sodium borohydride, in an alkanol solvent. To obtain the compounds which contain an esterified 3-hydroxy group, the amine as shown above is reacted with carbobenzoxy chloride to give the corresponding N-carbobenzoxy compound. This is then acylated using, for example, acetic anhydride to give the corresponding 3-acetoxy steroid. The N-carbobenzoxy protecting group is then removed by treatment with hydrogen bromide and acetic acid or by catalytic transfer hydrogenation. Alternatively, the 3-acetoxy group, or some other protected oxygen group such as a 3-(2-tetrahydropyranyloxy) group can be present on the steroid nucleus before the 17-imino group is introduced. In all cases, the product obtained is a secondary amine which can be converted to the corresponding N-methyl compound by treatment with formaldehyde and formic acid in an Eschweiler-Clarke reaction or by reaction with aqueous formaldehyde and sodium borohydride. Where the 3-hydroxy group is present in the form of an ester of a tetrahydropyran ether, these groups can be removed by standard procedures. That is, the ester group can be removed by base hydrolysis or the ether can be removed by treatment with dilute acid.

Those compounds wherein R' is $C_{2-4}$ alkyl can be obtained from a 17-cyclopropylamino steroid. This is reacted, for example, with acetyl chloride to give the corresponding acetamide which is then reduced with sodium cyanoborohydride to give the N-ethyl compound. In those cases where the above reaction with acetyl chloride also gives the 3-ester, the ester group can be removed, after the reduction, by base hydrolysis such as a combination of potassium carbonate, methanol and tetrahydrofuran or by acid hydrolysis such as with hydrochloric acid. In the latter case, the hydrochloride salt is obtained.

The 3-hydroxy-$\Delta^5$-compound obtained above can optionally be converted to the corresponding 3-keto-$\Delta^5$-compound by an Oppenauer oxidation using aluminum isopropoxide.

The imine starting material used in this process can be obtained by the reaction of an appropriate 4-substituted 3-oxygenated androst-5-en-17-one with the appropriate cyclopropylamine in refluxing methanol. The reaction is carried out in the presence of a dehydrating agent to remove water from the reaction mixture as it is formed. The term "3-oxygenated" used with regard to the starting material means that it can contain a free hydroxy group at the 3-position or the 3-hydroxy group can be present in the form of an ester with an alkanoic acid containing up to 6 carbon atoms or the 3-hydroxy group can be in the form of a protected alcohol group such as a tetrahydropyranyloxy group.

The 17-ketone referred to in the preceding paragraph can be obtained from the corresponding alcohol by oxidation with pyridinium chlorochromate in methylene chloride. Specifically, oxidation of 4,4-difluoro-3$\beta$-(2-tetrahydropyranyloxy)androst-5-en-17$\beta$-ol in this way gives 4,4-difluoro-3$\beta$-(2-tetrahydropyranyloxy)androst-5-en-17-one. To obtain the 4,4-difluoro-3$\beta$-(2-tetrahydropyranyloxy)androst-5-en-17$\beta$-ol, 4,4-difluoro-17$\beta$-hydroxyandrost-3-one is reacted with acetyl chloride in methylene chloride in the presence of triethylamine to give the corresponding 17-acetate ester which is then reduced using sodium borohydride in ethanol to give the corresponding 3$\beta$-hydroxy compound. This 3$\beta$-hydroxy compound is then reacted with dihydropyran and hydrogen chloride in methylene chloride to give the corresponding 3-(2-tetrahydropyranyloxy) compound which is then hydrolyzed using lithium hydroxide in a mixture of dioxane and water to give the desired 4,4-difluoro-3$\beta$-(2-tetrahydropyranyloxy)androst-5-en-17$\beta$-ol. Similar procedures can be used to obtain compounds having only one methyl or halogen substituent at the 4-position.

When the reduction referred to initially is carried out on an enamine, borane or a borohydride reducing agent such as sodium borohydride is used as the reducing agent. The necessary enamine starting material is obtained by the condensation of dehydroepiandrosterone with an appropriate secondary amine such as dicyclopropylamine. The alcohol final product obtained in this process can be acylated with an appropriate anhydride, such as acetic anhydride, to give the corresponding 3-acetoxy compound or it can be oxidized in an Oppenauer oxidation to give the corresponding 3-keto-$\Delta^5$-compound.

The present compounds are useful as inhibitors of steroid $C_{17-20}$lyase. The steroid $C_{17-20}$ lyase enzyme catalyzes the conversion of the $C_{21}$ steroids pregnenolone and progesterone to the $C_{19}$ steroids dehydroepiandrosterone and androstenedione, which are the precursors of the androgens, testosterone and 5$\alpha$-dihydrotestosterone. Androstenedione and testosterone, in turn, are the precursors of the estrogens, estrone and estradiol. Thus, inhibition of $C_{17-20}$ lyase by the present compounds can reduce formation of the estrogens as well as the androgens. Consequently, the present compounds are useful for treating various androgen-dependent disorders. The present invention thus also encompasses a method for treating androgen-dependent disorders which comprises administering to an individual suffering from such a disorder an effective amount of a compound of the present invention. More particularly, the present compounds are useful in the treatment of prostatic carcinoma, benign prostatic hyperplasia, male-pattern baldness and virilism and hirsutism (in women). The compounds of the present invention are also useful in the treatment of estrogen-dependent diseases, such as estrogen-dependent breast cancer.

It is well established that reduction of serum testosterone levels is useful in the treatment of many cases of prostatic carcinoma. In clinical practice, this has been accomplished by orchiectomy or by diethylstilbestrol treatment but the first approach is often psychologically unacceptable while a number of side effects are associated with the second approach. Thus, an alternative approach to testosterone reduction is desirable and this can be accomplished by the administration of the present compounds. To the extent that prostatic carcinoma is androgen-dependent, the present compounds would block the source of androgens and thus serve as an appropriate treatment for this condition.

The activity of the present compounds as inhibitors of steroid $C_{17-20}$ lyase is established using microsomal preparations of the steroid $C_{17-20}$ lyase enzyme from human or laboratory animal testes; human testes used for this purpose are obtained from therapeutic orchiectomies. The enzyme is incubated with NADPH and the test compound in the concentration range $5 \times 10^{-8}$ M to $3 \times 10^{-6}$ M and the extent of inhibition of the enzyme is determined with time-dependency of inhibition being established by a decline in enzyme activity with the time of exposure to the test compound. Time-dependency of inhibition often implies irreversible inactivation of the enzyme and irreversibility is specifically established by inability to restore enzyme activity by dialysis under conditions which maintained activity of native enzyme.

In the treatment of the various androgen-dependent disorders described earlier, the compounds of the present invention may be administered orally to the patient being treated to achieve the particular effect desired.

The amount of compound to be administered will vary over a wide range and can be any effective amount. Depending on the patient to be treated, and the severity of the condition being treated, the effective amount of compound administered will vary from about 0.625 to 62.5 mg/kg of body weight per day and preferably from 5 to 30 mg/kg of body weight per day. Unit dosages for oral administration may contain, for example, from 25 to 500 mg of a compound of the invention. Alternatively, the present compounds can be administered by parenteral routes or by implants.

In practicing the method of this invention, the active ingredient is preferably incorporated in a composition containing a pharmaceutical carrier and from about 5 to about 90% by weight of the cyclopropylamino steroid or a pharmaceutically-acceptable salt thereof. The term "pharmaceutical carrier" refers to known pharmaceuticals excipients useful in formulating pharmaceutically active compounds for internal administration to animals, and which are substantially non-toxic and non-sensitizing under conditions of use. The compositions can be prepared by known techniques for the preparation of tablets or capsules and can contain suitable excipients known to be useful in the preparation of the particular type of composition desired. Suitable pharmaceutical carriers in formulation techniques are found in standard texts, such as *Remingtons Pharmaceutical Sciences*, Mack Publishing Company, Easton, Pennsylvania.

The following examples are presented to illustrate the present invention but they should not be construed as limiting it in any way.

EXAMPLE 1

To a solution of 21 g of 4,4-difluoro-3β-(2-tetrahydropyranyloxy)androst-5-en-17-one in a mixture of 175 ml of cyclopropylamine and 150 ml of methanol there is added 5 g of molecular sieves. The reaction mixture is refluxed for 48 hours, cooled to room temperature, and filtered through magnesium sulfate. The magnesium sulfate is washed with ethyl acetate and the solvent is removed from the combined filtrates under reduced pressure to give 17-(cyclopropylimino)-4,4-difluoro-3β-(2-tetrahydropyranyloxy)androst-5-ene.

EXAMPLE 2

To a solution of 9.1 g of 17-(cyclopropylimino)-4,4-difluoro-3β-(2-tetrahydropyranyloxy)androst-5-ene in 200 ml of dry ethanol is added 2 g of sodium borohydride. The reaction mixture is stirred at room temperature for 3 hours and then 100 ml of solvent is removed from the mixture under reduced pressure. The reaction mixture is then quenched with dilute acetic acid, diluted with 600 ml of water, and the pH is adjusted to 14 by the addition of sodium hydroxide. The aqueous mixture is extracted 3 times with 600 ml potions of ethyl acetate and the combined organic extracts are dried over magnesium sulfate. Removal of the solvent under reduced pressure gives the desired 17β-(cyclopropylamino)-4,4-difluoro-3β-(2-tetrahydropyranyloxy)androst-5-ene as a white solid. This material is treated with a catalytic amount of hydrochloric acid in dioxane to remove the tetrahydropyranyl protecting group. This compound has the following structural formula:

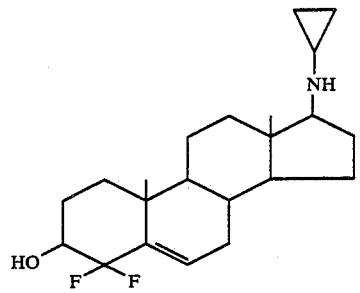

EXAMPLE 3

Reaction of 4,4-difluoro-3β-(2-tetrahydropyranyloxy)-androst-5-en-17-one with 1-methylcyclopropylamine according to the procedure described in Example 1 gives 4,4-difluoro17-(1-methylcyclopropylimino)-3β-(2-tetrahydropyranyloxy)androst-5-en-3β-ol. This is then reduced with sodium borohydride and the tetrahydropyranyl group is removed according to the procedure described in Example 2 to give 4,4-difluoro-17β-(1-methylcyclopropylamino)androst-5-en-3β-ol.

EXAMPLE 4

Reaction of 17-(cyclopropylimino)-4,4-difluoro-3-(2-tetrahydropyranyloxy)androst-5-en-3β-ol with an excess of acetic anhydride in the presence of a base (pyridine) followed by removal of the excess anhydride and acetic acid gives 3β-acetoxy-17-(cyclopropylimino)-4,4-difluoro-3-(2-tepyranyloxy)androst-5-ene. Reduction of this ester with sodium borohydride and removal of the tetrahydropyranyl group according to the procedure described in Example 2 gives 3β-acetoxy-17β-(cyclopropylamino)-4,4-difluoroandrost-5-ene. 3β-(Cyclopentanepropionyloxy)-17β-(cyclopropylamino)-4,4-difluoroandrost-5-ene and 3β-(benzenepropionyloxy)-17β-(cyclopropylamino)-4,4-difluoroandrost-5-ene are obtained in a similar way using the appropriate acid chlorides.

EXAMPLE 5

To a mixture of 10 ml of formic acid and 5 ml of formaldehyde is added 1.4 g of 17β-(cyclopropylamino)-4,4-difluoroandrost-5-en-3β-ol. The mixture is heated at reflux for 5 hours, the volume is then reduced to 7.5 ml in vacuo, and 10 ml of 50% (w/w) aqueous sodium hydroxide is added. The aqueous layer is separated and extracted with ethyl acetate and the combined organic solutions are dried over magnesium sulfate. The solvent is then removed in vacuo and the residual product is purified by flash chromatography to give 4,4-difluoro-17β-[N-methyl(cyclopropylamino)-]androst-5-en-3β-ol.

EXAMPLE 6

A solution of 1.5 grams of 17β-(cyclopropylamino)-4,4-difluoroandrost-5-en-3β-ol in 80 ml of toluene is concentrated to 75% of its original volume and 20 ml of cyclohexanone is added. The mixture is again concentrated to 75% of its volume and 1.5 g of aluminum isopropoxide is added. The reaction mixture is refluxed for 45 minutes, cooled to room temperature, and 50 ml of water and 5 ml of concentrated hydrochloric acid are added. The solution is then treated with 11 g of sodium hydroxide and the two phases are separated. The aqueous phase is extracted with 50 ml of ethyl acetate and the combined organic extracts are dried over sodium sulfate. The solvent is removed in vacuo and crystallization of the residue from hexane/ethyl acetate gives 17β-(cyclopropylamino)-4,4-difluoroandrost-5-en-3-one.

What is claimed is:

1. A compound of the formula

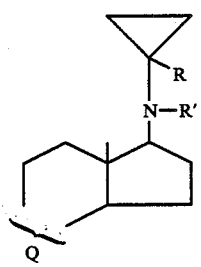

wherein R is hydrogen or methyl; R' is hydrogen, $C_1$-$C_4$ alkyl or cyclopropyl; and Q is

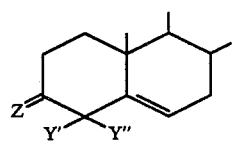

or

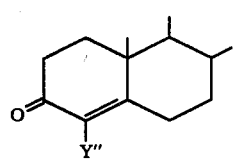

wherein Z is =O, β—OH or β—OZ' wherein Z' is alkanoly of 1-10 carbon atoms or substituted $C_{2-4}$ alkanyol wherein the substitutent is cyclopentane or benzene; Y' is hydrogen or halogen; and Y" is methyl or halogen.

2. A compound according to claim 1 which has the formula:

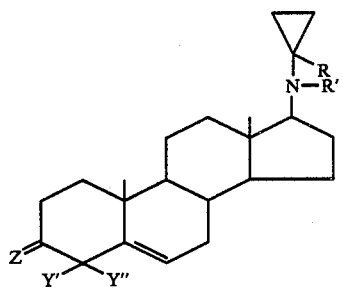

wherein Z is =O, β—OH or β—OZ' wherein Z' is alkanoly of 1-10 carbon atoms or substituted $C_{2-4}$ alkanyol wherein the substitutent is cyclopentane or benzene; R is hydrogen or methyl; R' is hydrogen or $C_1$-$C_4$ alkyl; Y' is halogen; and Y" is methyl or halogen.

3. A compound according to claim 1 which has the formula:

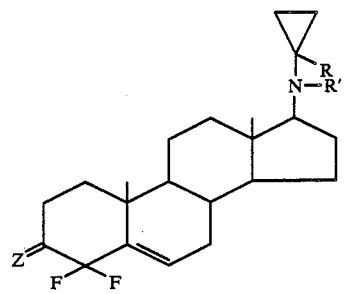

wherein Z is =O, β—OH or β—OZ' wherein Z' is alkanoly of 1-10 carbon atoms or substituted $C_{2-4}$ alkanyol wherein the substitutent is cyclopentane or benzene; R is hydrogen or methyl; R' is hydrogen or $C_1$-$C_4$ aklyl.

4. A compound according to claim 1 which is 17β-(cyclopropylamino)-4,4-difluoroandrost-5-en-3β-ol.

5. A compound according to claim 1 which is 17β-(cyclopropylamino)-4,4-difluoroandrost-4-en-3-one.

6. A method for treating androgen-dependent disorders which comprises administering to an individual suffering from such a disorder an effective amount of a compound of the formula

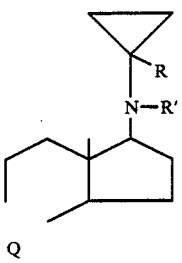

wherein R is hydrogen or methyl; R' is hydrogen, $C_1$-$C_4$ alkyl or cyclopropyl; and Q is

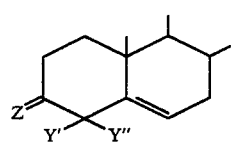

or

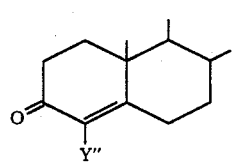

wherein Z is =O, β—OH or β—OZ' wherein Z' is alkanoyl of 1-10 carbon atoms or substituted $C_{2-4}$ alkanoyl wherein the substituent is cyclopentane or benzene; Y' is hydrogen or halogen; and Y" is methyl or halogen.

7. A method according to claim 6 for treating androgen-dependent disorders which comprises administering to an individual suffering from such a disorder an effective amount of a compound of the formula:

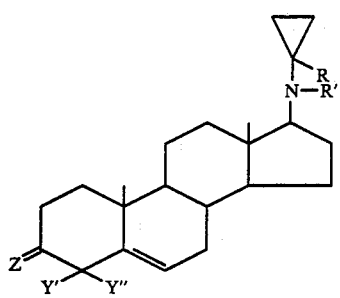

wherein Z is =O, β—OH or β—OZ' wherein Z' is alkanoly of 1-10 carbon atoms or substituted C$_{2-4}$ alkanyol wherein the substitutent is cyclopentane or benzene; R is hydrogen or methyl; R' is hydrogen or C$_1$-C$_4$ aklyl; Y' is halogen; and Y" is methyl or halogen.

8. A method according to claim 6 which comprises administering an effective amount of 17β-(cyclopropylamino)-4,4-difluoroandrost-5-en-3β-ol.

* * * * *

UNITED STATES PATENT AND TRADEMARK OFFICE
CERTIFICATE OF CORRECTION

PATENT NO. : 4,966,898  
DATED : October 30, 1990  
INVENTOR(S) : Michael R. Angelastro, Thomas R. Blohm Page 1 of 2

It is certified that error appears in the above-identified patent and that said Letters Patent is hereby corrected as shown below:

Column 1, Line 24 patent reads:

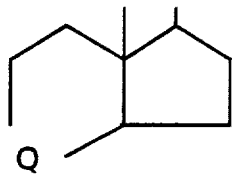

and should read:

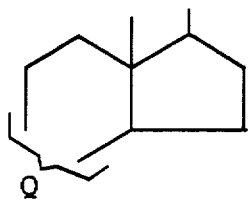

At Column 1, Line 46 patent reads: "alkanoly" and should read: --alkanoyl--.
At Column 2, Line 51 patent reads:

At Column 6, Line 33 patent reads: "(2-tepyranyloxy)" and should read: -- (2-tetrahydropyranyloxy)--.
At Column 7, Line 41 patent reads: "alkanoly" and should read: --alkanoyl--.
At Column 7, Line 41 patent reads: "$C_{2-4}$ alkanyol" and should read: --$C_{2-4}$ alkanoyl--.
At Column 7, Line 62 patent reads: "alkanoly" and should read: --alkanoyl--.
At Column 7, Line 63 patent reads: "alkanyol" and should read: --alkanoyl--.
At Column 8, Line 16 patent reads: "alkanoly" and should read: --alkanoyl--.
At Column 8, Line 17 patent reads: "alkanyol" and should read: --alkanoyl--.

UNITED STATES PATENT AND TRADEMARK OFFICE
CERTIFICATE OF CORRECTION

PATENT NO. : 4,966,898

DATED : October 30, 1990

INVENTOR(S) : Michael R. Angelastro, Thomas R. Blohm

It is certified that error appears in the above-identified patent and that said Letters Patent is hereby corrected as shown below:

At Column 8, Line 19 patent reads: "aklvl" and should read: --alkyl--.
At Column 8, Line 37 patent reads and should read:

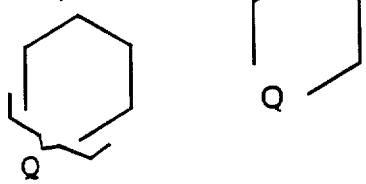

At Column 10, Line 2 patent reads: "alkanoly" and should read: --alkanoyl--.
At Column 10, Line 3 patent reads: "alkanyol" and should read: --alkanoyl--.
At Column 10, Line 6 patent reads: "aklyl" and should read: --alkyl--.

Signed and Sealed this

Seventeenth Day of March, 1992

Attest:

HARRY F. MANBECK, JR.

*Attesting Officer*  *Commissioner of Patents and Trademarks*